(12) United States Patent
Kowarschik et al.

(10) Patent No.: US 11,373,310 B2
(45) Date of Patent: Jun. 28, 2022

(54) METHOD FOR PRODUCING A DIGITAL SUBTRACTION ANGIOGRAPHY AND APPARATUS

(71) Applicant: Siemens Healthcare GmbH, Erlangen (DE)

(72) Inventors: Markus Kowarschik, Nuremberg (DE); Sebastian Schafer, Madison, WI (US)

(73) Assignee: Siemens Healthcare GmbH, Erlangen (DE)

( * ) Notice: Subject to any disclaimer, the term of this patent is extended or adjusted under 35 U.S.C. 154(b) by 34 days.

(21) Appl. No.: 17/004,489

(22) Filed: Aug. 27, 2020

(65) Prior Publication Data

US 2021/0090256 A1    Mar. 25, 2021

Related U.S. Application Data

(60) Provisional application No. 62/904,897, filed on Sep. 24, 2019.

(30) Foreign Application Priority Data

Oct. 16, 2019   (DE) .......................... 102019215904.4

(51) Int. Cl.
*G06K 9/00*    (2022.01)
*G06T 7/00*    (2017.01)
(Continued)

(52) U.S. Cl.
CPC ............ *G06T 7/0014* (2013.01); *A61B 6/481* (2013.01); *A61B 6/504* (2013.01); *G06T 7/11* (2017.01);
(Continued)

(58) Field of Classification Search
CPC ....... G06T 7/0014; G06T 7/11; G06T 11/001; G06T 2207/10121; G06T 2207/30101; A61B 6/481; A61B 6/504
See application file for complete search history.

(56) References Cited

U.S. PATENT DOCUMENTS

2007/0055148 A1    3/2007  Klingenbeck-regn
2010/0061608 A1*   3/2010  Galant ..................... G06T 7/11
                                                          382/128
(Continued)

FOREIGN PATENT DOCUMENTS

DE    102005042328 A1    3/2007
DE    102009014765 A1    10/2010
DE    102014201556 A1    7/2015

OTHER PUBLICATIONS

German Office Action for German Application No. 10 2019 215 904.4 filed Aug. 14, 2020.

*Primary Examiner* — Atiba O Fitzpatrick
(74) *Attorney, Agent, or Firm* — Lempia Summerfield Katz LLC (57) ABSTRACT

For a particularly comprehensive identification of hollow organ systems, a method is provided for producing a digital subtraction angiography of a hollow organ system of a patient. The method includes: providing mask image data recorded by an X-ray device; providing at least first fill image data recorded by the X-ray device, which has been recorded during an at least partial filling of the hollow organ system with a contrast agent; starting from a first intravenous and a second intraarterial contrast agent injection following in time; ascertaining at least first subtraction image data by subtracting the mask image data from the at least first fill image data; ascertaining final subtraction image data from the at least first subtraction image data; and segmenting the final subtraction image data and assigning
(Continued)

the pixels or voxels of the final subtraction image data to at least two different intensity classes based on their respective intensity value.

17 Claims, 3 Drawing Sheets

(51) Int. Cl.
*G06T 7/11* (2017.01)
*G06T 11/00* (2006.01)
*A61B 6/00* (2006.01)

(52) U.S. Cl.
CPC .. *G06T 11/001* (2013.01); *G06T 2207/10121* (2013.01); *G06T 2207/30101* (2013.01)

(56) References Cited

U.S. PATENT DOCUMENTS

| | | | |
|---|---|---|---|
| 2015/0150526 A1* | 6/2015 | Oh | A61B 6/469 |
| | | | 378/62 |
| 2015/0173699 A1* | 6/2015 | Kyriakou | A61B 6/501 |
| | | | 378/62 |
| 2015/0208996 A1* | 7/2015 | Kyriakou | A61B 6/481 |
| | | | 600/431 |
| 2015/0325011 A1 | 11/2015 | Ashida | |
| 2018/0211422 A1* | 7/2018 | Qiu | G06T 7/0016 |

\* cited by examiner

METHOD FOR PRODUCING A DIGITAL SUBTRACTION ANGIOGRAPHY AND APPARATUS

The present patent document claims the benefit of U.S. Provisional Patent Application No. 62/904,897, filed Sep. 24, 2019, and German Patent Application No. 10 2019 215 904.4, filed Oct. 16, 2019, which are hereby incorporated by reference.

TECHNICAL FIELD

The disclosure relates to a method for producing a digital subtraction angiography of a hollow organ system of a patient in accordance as well as an apparatus for performing a method of this kind.

BACKGROUND

Digital subtraction angiography (DSA) may serve to examine blood vessels or hollow organs. In one example, two-dimensional variants, temporally successive (two-dimensional) projection images of a vascular system of a patient to be examined are produced by an X-ray angiography system (e.g., by a C-arm system), during which time a contrast agent is injected. This results in one projection image without contrast agent, also known as the mask image, and further projection images with a distribution of contrast agent in the vascular system, known as projection fill images. The digital mask image is subtracted from the subsequent projection fill images. What remain are merely the parts that differ, e.g., specifically the vascular system.

Three-dimensional digital subtraction angiography (3D DSA) allows a high-resolution representation, e.g., of contrast-enhanced vascular systems as 3D volumes. To this end, a mask run without contrast agent and a fill run with contrast agent may be performed, and a series of projection images are compiled in each case. Here, the two-dimensional projection images may originate from a recording protocol of a C-arm X-ray device (e.g., cone beam CT) rotating around the patient. The series of projection mask images may be removed from the series of projection fill images and the resulting series of two-dimensional subtraction images may be reconstructed to form a three-dimensional subtraction angiography image. Four-dimensional (4D) DSA refers to time-resolved 3D digital subtraction angiography.

For the diagnosis and treatment of clinical conditions, a particularly good and precise representation of vascular systems in organs, (e.g., the brain, the heart, or the liver), is required. In this context, it is important that both arterial and venous vascular systems are represented. For various applications, it is becoming ever more important that the venous vascular system in the brain may be represented in an exact manner. This is the case, for example, in the treatment of what are known as AVMs (arteriovenous malformations), a knot-like malformation of the vessels, in which arteries are directly connected to the veins without capillaries. In AVMs in the brain, there is a great risk of a rupture with severe brain hemorrhaging due to the high pressure in the vessels, for example. For preventative treatment of an AVM, for example, a venous AVM embolization is performed, in which, under X-ray observation, an embolisate is injected into the vessel within the AVM, which closes off the vessel. In order to perform such an intervention, a comprehensive image of the cerebral vascular system must be available, and it is also necessary to identify the artery(ies) supplying the AVM and in particular the draining vein(s) (as these are more difficult to ascertain).

By known DSA methods, although it is possible to represent the cerebral vascular system, it may be difficult to detect the artery(ies) supplying the AVM and the vein(s) draining the AVM from the many arteries represented.

SUMMARY AND DESCRIPTION

The object of the present disclosure is to provide a method for producing a digital subtraction angiography of a hollow organ system of a patient, which enables an identification of vein(s) draining the AVM and artery(ies) supplying the AVM. Furthermore, the object of the disclosure is to provide an apparatus suitable for performing the method.

The object is achieved by a method for producing a digital subtraction angiography of a hollow organ system of a patient and by an apparatus as disclosed herein.

The scope of the present disclosure is defined solely by the appended claims and is not affected to any degree by the statements within this summary. The present embodiments may obviate one or more of the drawbacks or limitations in the related art.

The method for producing a digital subtraction angiography of a hollow organ system of a patient includes the following acts: providing mask image data recorded by an X-ray device; providing at least first fill image data recorded by the X-ray device, which has been recorded during an at least partial filling of the hollow organ system with a contrast agent; starting from a first intravenous and a second intraarterial contrast agent injection following in time; ascertaining at least first subtraction image data by subtracting the mask image data from the at least first fill image data; ascertaining final subtraction image data from the at least first subtraction image data; and segmenting the final subtraction image data and assigning the pixels or voxels of the final subtraction image data to at least two different intensity classes based on their respective intensity value.

By way of the method, particularly in the case in which the contrast agent injections which have taken place previously are appropriate in terms of location and timing, it is possible both to produce a comprehensive image of the desired hollow organ system and, through the division into a plurality of intensity classes, to give a clear indication of particular draining veins and supply arteries. The disclosure is based on the fact that, due to the contrast agent, particularly highly perfused hollow organs have a particularly high intensity value on an X-ray image, at least for a brief time. As there are no capillaries between arteries and veins in the AVM, the perfusion from the arteries into the veins is exceptionally high here. For a physician charged with the diagnosis and treatment, (e.g., of an AVM), this information is of great relevance and may contribute to a considerably improved care of the patient. Thus, for example, by way of the DSA resulting from the method, in the case of an AVM in the brain of a patient, it becomes clearly evident to the physician which vein(s) are draining the AVM and which artery(ies) are supplying the AVM, so that the physician is subsequently able to perform a treatment, (e.g., in the form of an embolization), safely and correctly. The injection site of the first, intravenous injection of contrast agent which has previously taken place may be an arm vein, for example, and the injection site of the second, intraarterial injection may be an intracerebral artery.

According to an embodiment, the first subtraction image data is used as the final subtraction image data. This is advantageous in the case in which solely the first subtraction image data is present.

According to a further embodiment, the following acts are performed: providing at least first and second fill image data recorded by the X-ray device, which have been recorded during an at least partial filling of the hollow organ system with a contrast agent; starting from a first intravenous and a second intraarterial contrast agent injection following in time; ascertaining at least first and second subtraction image data by subtracting the mask image data from the at least first and second fill image data; and ascertaining final subtraction image data from the at least first and second subtraction image data by determining the maximum intensity value of the corresponding pixel or voxel of the at least first and second subtraction image data as the intensity value of each pixel or voxel of the final subtraction image data.

In the case in which at least first and second fill image data, (e.g., two or more sets of fill image data), are present, then advantageously in each case the maximum intensity value is selected from all subtraction image data for each pixel or voxel and used for the final subtraction image data. Therefore, if, in the first subtraction image data, for example, the intensity value for a particular pixel is lower than in the second subtraction image data, then the intensity value of the second subtraction image data is used as the final value. In this manner, the intensity values are compared for all pixels or voxels of the image data, and subsequently the maximum intensity value is selected in each case. The final subtraction image data is therefore composed of the maximum intensity values for all the pixels/voxels of the hollow organ system in each case. This makes it possible to produce a comprehensive image of the hollow organ system regardless of the temporally individual fill level of the respective fill image data. Therefore, a kind of time-independent fill image is produced, which then shows the physician a systematic overview of the overall hollow organ system. It is also possible for more than two sets of fill image data to be available. Also, in this example, the maximum intensity value is then selected from three or more values for each pixel/voxel. Because, due to the contrast agent, particularly highly perfused hollow organs have a particularly high intensity value on an X-ray image, at least for a brief time, a particularly good overview of the hollow organ system may be produced by using the maximum intensity value.

According to a further embodiment, the mask image data is formed of at least one series of projection mask images and the at least first and/or second fill image data is formed of at least one first and/or second series of projection fill images. Additionally, the series of projection mask images are reconstructed to form a mask volume and the at least first and/or second series of projection fill image are reconstructed to form at least one first and/or second fill volume. Further, at least one first and/or second subtraction volume is ascertained by subtracting the mask volume from at least the first and/or the second fill volume. Also, a final subtraction volume is ascertained from at least the first and/or second subtraction volume, and wherein the final subtraction volume is segmented. Additionally, the voxels of the final subtraction volume are assigned to at least two different intensity classes based on their respective intensity value. In addition to 2D, the method may be performed as 3D and even 4D DSA. In particular, the at least one series of projection mask images and the at least one first and/or second series of projection fill images have been recorded during at least one rotational run of a recording system around the patient in each case. The projection images are recorded during rotational runs of a C-arm around the patient, for example, as 3D DSA. In this context, this may involve cone beam CT runs, for example. According to an embodiment, for example, projection image data is available from two successive mask runs (200±x degrees forward and backward) and fill image data from three fill runs following the mask runs (200±x degrees, backward and forward again).

As an alternative, also in 3D DSA, first the subtraction of the 2D image data from one another and then the reconstruction of the image series to form volumes may be performed. According to a further embodiment, the mask image data is formed of at least one series of projection mask images and the at least first and (or) second fill image data is formed of at least one first and (or) second series of projection fill images. Also, at least one first and (or) second series of subtraction images are ascertained by subtracting the series of projection mask images from at least the first and (or) the second series of projection fill images. Further, the at least one first and (or) second series of subtraction images are reconstructed to form at least one first and (or) second subtraction volume. Additionally, a final subtraction volume is ascertained from at least the first and (or) second subtraction volume. Also, the final subtraction volume is segmented, and the voxels of the final subtraction volume are assigned to at least two different intensity classes based on their respective intensity value.

According to a further embodiment, the at least two intensity classes are differentiated through the use of at least one intensity threshold value. When differentiating into two intensity classes, for example, precisely one threshold value is therefore selected or is already preset. All pixels or voxels with an intensity value lying below the threshold value belong to the first intensity class, and all pixels or voxels with an intensity value lying above the threshold value belong to the second intensity class. For differentiation purposes, for example, an image processing unit is used with an algorithm which categorizes the intensity values into the intensity classes. Three or more intensity classes may also be used, which are then differentiated by two or more threshold values.

Advantageously, in order for a user to be able to identify the different intensity classes particularly well, the digital subtraction angiography of the hollow organ system is displayed on a display unit, wherein the parts of the hollow organ system which are assigned to different intensity classes are marked with different colors. Thus, it may be provided, for example, that all pixels or voxels which are assigned to the first intensity class are colored a first color, (e.g., green), and all pixels or voxels which are assigned to the second intensity class are colored a second color, (e.g., red).

The disclosure additionally claims an apparatus for performing the method. The apparatus includes an image processing unit, in particular, with at least one image editing algorithm, configured for ascertaining subtraction image data by subtracting mask image data from fill image data, for ascertaining final subtraction image data and for segmenting final subtraction image data and assigning pixels or voxels of the final subtraction image data to at least two different intensity classes based on their respective intensity value, as well as having a memory unit for storing image data. The apparatus advantageously has an X-ray device, (e.g., a C-arm X-ray device), which is configured for recording mask image data and fill image data of a hollow organ system of a patient. Additionally, the apparatus may expediently have a contrast agent injection apparatus with at least two injectors arranged such that they are spaced apart, wherein the first injector is configured for the triggered intravenous injection of contrast agent and the second injector for the intraarterial injection of contrast agent following in time, and with a trigger apparatus for the automatic, controlled activation of the two injectors. The apparatus may additionally have a system controller for actuating the X-ray device, the image processing unit, and the contrast agent injection apparatus.

BRIEF DESCRIPTION OF THE DRAWINGS

The disclosure and further advantageous embodiments according to features of the subclaims are explained in greater detail below based on schematically illustrated exemplary embodiments in the drawing, without thereby limiting the disclosure to these exemplary embodiments. In the drawings:

DETAILED DESCRIPTION

Figure 1:
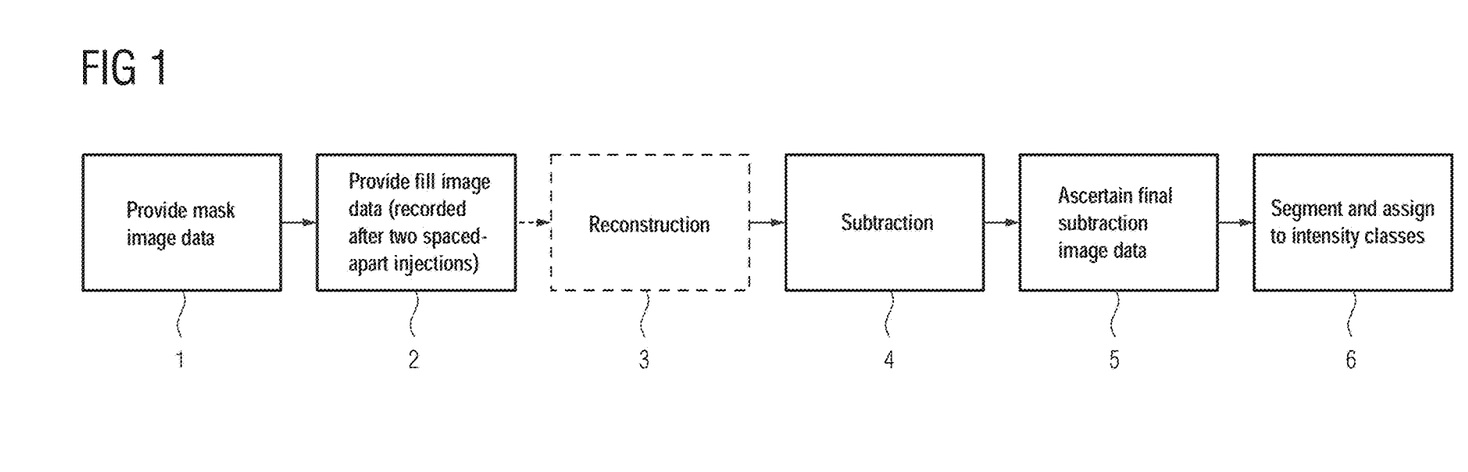
FIG. 1 depicts a sequence of acts of a method according to the embodiment.

In FIG. 1, a sequence is shown of certain acts of a method for producing a digital subtraction angiography of a hollow organ system of a patient. The hollow organ system may, for example, involve a cerebral vascular system or also a vascular system in the heart or liver or another organ of a patient. By way of the method, the desired vascular system may be represented comprehensively and particularly highly perfused vessels, (e.g., AVM-draining veins), may be identified.

Figure 2:
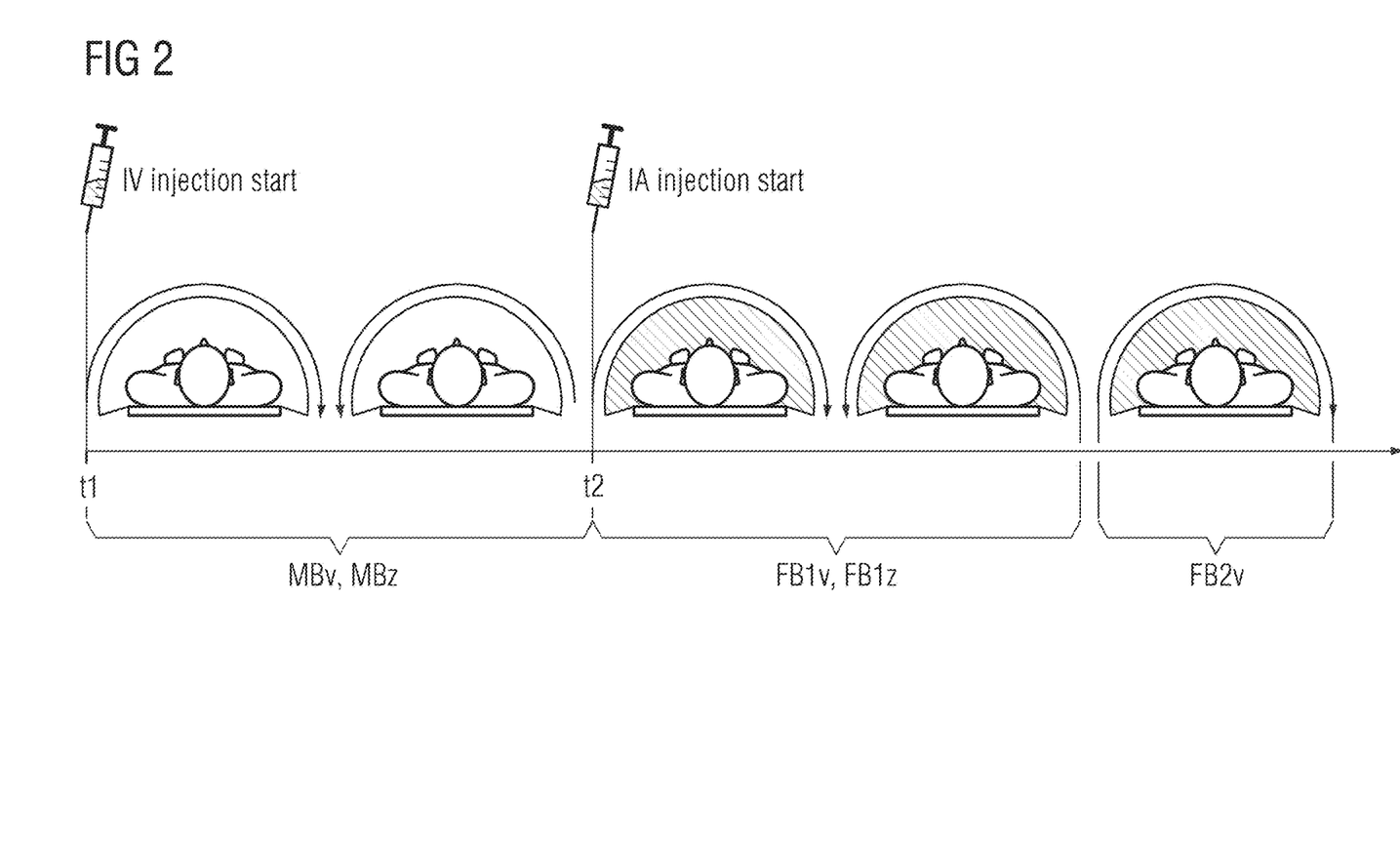
FIG. 2 depicts a view of an example of an acquisition protocol for recording the image data provided for the method.

In act 1, mask image data of the hollow organ system recorded by an X-ray device is provided and, in act 2, at least first fill image data is provided which has been recorded by the same X-ray device during an at least partial filling of the hollow organ system with a contrast agent, starting from a first intravenous and a second intraarterial contrast agent injection following in time. Depending on the application, the image data may involve 2D, 3D, or 4D image data. An exemplary 4D DSA acquisition protocol for producing mask image data and fill image data is shown in FIG. 2 and is described in more detail further below. In 2D DSA, the mask image data involves individual projection mask images and the fill image data involves individual projection fill images, while 3D DSA involves series of projection mask images and series of projection fill images. 4D DSA involves time-resolved 3D DSA, in which the temporal information is generated by 2D image data based on 3D DSA image data.

In a possible embodiment of the method, first mask image data and first and second fill image data are provided. It is also possible for two or more sets of mask image data and three or more sets of fill image data to be provided.

In act 3, which is optional or only occurs in the case of 3D or 4D DSA, the (e.g., at least first) series of projection mask images is reconstructed to form a mask volume, (at least) the first series of projection fill images is reconstructed to form a first fill volume and (if present) the second series of projection fill images is reconstructed to form a second fill volume. In this context, known reconstruction algorithms are used.

In act 4, first and second subtraction image data is ascertained by subtracting the mask image data from the at least first and second fill image data. In the 3D case, therefore, a first and a second subtraction volume is ascertained by subtracting the mask volume from the first and the second fill volume. If only first fill image data is available, then only first subtraction image data is also produced. If three or more instances of fill image data are available, then three or more instances of subtraction image data are also produced.

In act 5, final subtraction image data is ascertained from all available subtraction image data. If there is only first subtraction image data (e.g., a subtraction volume), then this is ascertained as final subtraction image data (e.g., final subtraction volume). If first and second subtraction image data (e.g., a first and a second subtraction volume) are available, then the maximum intensity value of the corresponding pixel or voxel of the first and second subtraction image data is chosen and used as the intensity of each pixel or voxel of the final subtraction image data. In the case of a low and a high intensity value, then the high intensity value is therefore used. Therefore, an image or volume is generated from the maximum intensity values. If three or more, e.g., subtraction volumes are available, then the maximum intensity value is chosen and used from all those available. Following this act, a comprehensive mapping of the hollow organ system of the examined organ, (e.g., brain), is already produced. The final subtraction image data, (e.g., final subtraction volume), may be displayed on a display unit.

In act 6, the final subtraction image data (e.g., final subtraction volume) is segmented and the pixels or voxels of the final subtraction image data (e.g., the final subtraction volume) are assigned to at least two different intensity classes based on their respective intensity value. The segmentation and assignment may be performed, e.g., by way of a known segmentation method, for example, a known clustering algorithm (e.g., k-means algorithm). The at least two intensity classes may be differentiated, e.g., through the use of at least one intensity threshold value. The intensity threshold value may be set or selected beforehand, or not until the running of the method. It may be selected automatically or manually. The final subtraction image data, (e.g., final subtraction volume), may be displayed in segmented form on a display unit. Therefore, for example, the parts of the hollow organ system assigned to different intensity classes may be marked in different colors. Thus, it may be provided, for example, that all pixels or voxels which are assigned to a first intensity class are colored a first color, (e.g., green), and all pixels or voxels which are assigned to a second intensity class are colored a second color, (e.g., red). In this manner, it is particularly easy for a user to identify which parts of the vascular system are systemic and which are fed by the (e.g., cerebral) artery, into which the second injection has been made. In this manner, for example, AVM-draining veins and AVM-supplying arteries may be made visible.

FIG. 2 shows an exemplary 4D DSA acquisition protocol for producing the mask image data and fill image data. One such protocol, or a similar protocol, has been performed before the actual method, in order to record the corresponding mask image data and fill image data. The projection images are recorded during rotational runs of a C-arm of an (e.g., angiography) X-ray device around the patient, in particularly around the organ to be represented. In this context, this may involve cone beam CT runs, for example. The exemplary protocol is composed of two successive mask runs (e.g., MBv+z; 200+x degrees forward and backward) and three fill runs following the mask runs (e.g., FB1v+z and FB2v; 200+x degrees forward and backward and forward again). Three fill runs are performed, in order to cover a particularly long period of time for the 4D DSA. For a normal 3D DSA, for example, one mask run and one fill run is sufficient. The duration of each individual run may amount to 5 seconds, for example.

First, at a first point in time t1, a first injection is started, e.g., by the first injector for intravenous injection of a contrast agent being activated. The injector may be situated in a peripheral vein (e.g., arm vein). At approximately the same time as the first injection, a mask run is started forward (in this example, forward and backward relate to the direction of the rotation around the patient), from which a first series of projection mask images (MBv) e.g., of a brain of a patient is obtained. Directly following this, the mask run is performed backward, from which a second series of projection mask images (MBz) of the brain is recorded. If both mask runs each last approximately 5 seconds, then the vessels of the brain are not yet filled with the contrast agent, as it may take approximately 10 seconds for the contrast agent to reach the brain. Directly following the mask runs, at a second point in time t2, e.g., approximately 10 seconds after the first point in time t1, a second injection is started, e.g., by the second injector for intraarterial injection of a contrast agent being activated.

This second injector may be situated in a cerebral artery, e.g., a supply artery of an AVM to be represented. A carotid artery may be used, for example. At approximately the same time as the second injection, three fill runs are performed in sequence: first fill run forward, from which a first series of projection fill images (FB1v) emerge, a first fill run backward, from which a second series of projection fill images (FB1z) emerge, and a second fill run forward, from which a third series of projection fill images (FB2v) emerge.

While the three fill runs (e.g., each approximately 5 seconds, or approximately 15 seconds in total) are being performed, it may be expected that the contrast agent from the first injection is spreading in the vascular system of the brain and an exceptionally large amount of contrast agent from the second injection flows from the supplying artery of the AVM into the corresponding vein. In particular protocols, it may make sense to subtract image data from comparable runs (e.g., fill run forward minus mask run forward and fill run backward minus mask run backward) during a later subtraction of fill image data and mask image data. In reconstructed volumes, this may not be necessary. For example, both injections may be performed with the same contrast agent. Other acquisition protocols are also possible, e.g., with only one or at least three mask runs and one, two or at least four fill runs, other durations, more injections, other organs, etc. Comparably, 4D DSA recording protocols may also be performed. In 2D DSA recording protocols, only individual projection images are made, without rotational runs. The sequence is comparable to 3D DSA.

The respective acquisition protocol may be actuated automatically by a system controller.

Figure 3:
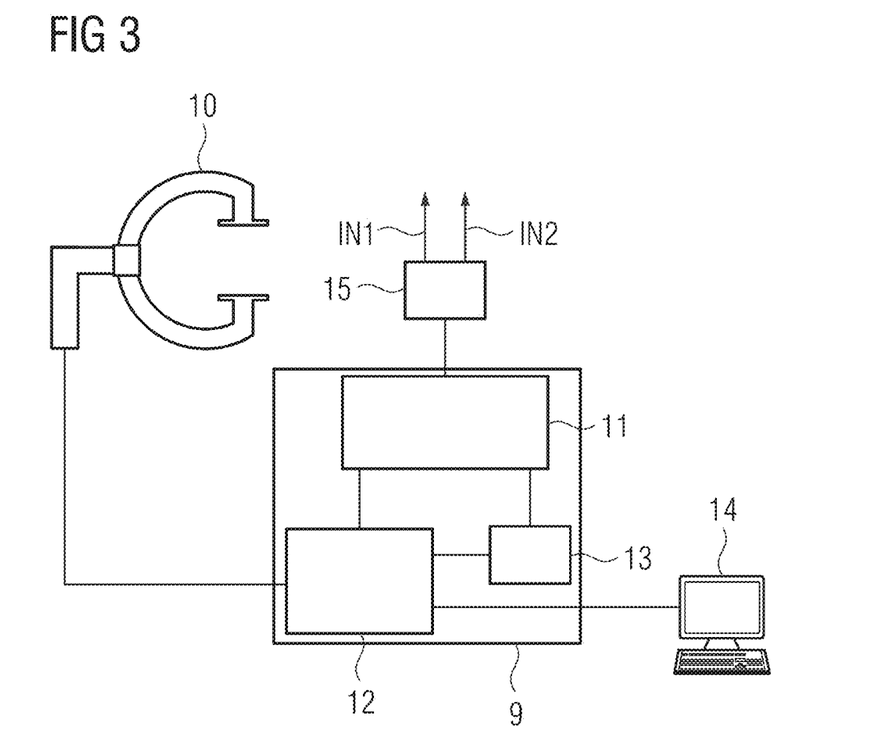
FIG. 3 depicts a view of an example of a C-arm X-ray device for performing the method.

An apparatus 9 suitable for performing the method is shown, for example, in FIG. 3. The apparatus 9 has an image processing unit 12, in particular, with at least one image editing algorithm. The image processing unit is embodied for ascertaining subtraction image data by subtracting mask image data from fill image data, for ascertaining final subtraction image data, and for segmenting final subtraction image data and assigning pixels or voxels of the final subtraction image data to at least two different intensity classes based on their respective intensity value. Additionally, the apparatus has a memory unit 13 for storing image data. The apparatus 9 advantageously includes an X-ray device, (e.g., a C-arm X-ray device 10), which is configured for recording mask image data and fill image data of a hollow organ system of a patient.

The C-arm X-ray device may have a C-arm configured to record series of projection images during rotational runs of the C-arm around the patient. Additionally, the apparatus 9 may have a contrast agent injection apparatus with at least two injectors IN1 and IN2 arranged such that they are spaced apart, wherein the first injector IN1 is embodied for the automatically triggered intravenous injection of contrast agent and the second injector IN2 for the automatically triggered intraarterial injection of contrast agent following in time, and with a trigger apparatus 15 for the automatic, controlled activation of the two injectors. The apparatus 9 also has a system controller 11 for actuating the X-ray device 10, the image processing unit 12, and the contrast agent injection apparatus. Additionally, the apparatus 9 has a display unit 14 for displaying image data.

The acquisition protocol described in FIG. 2, or another, similar acquisition protocol, may be actuated in a fully automatic manner by an apparatus 9.

The disclosure describes a method for producing a DSA, which, following a multi-injection recording protocol with at least a first intravenous and a second intraarterial injection (the latter in particular taking place in an artery supplying an AVM), illustrates an option of both representing the entire hollow organ system, e.g., of the brain and highlighting particularly noticeable connecting vessels between the overall system and, e.g., an AVM in the brain. In particular, the contribution of an individual vessel (e.g., of one of the two carotid arteries) may also be identified. The image produced, which is multi-level with regard to Hounsfield units (HU), is segmented and differences may be represented in a manner which is clearly visible to a physician. This produces the opportunity for the physician to develop an appropriate strategy for treatment, e.g., in the case of AVMs in the brain or venous stenosis.

The disclosure may be briefly summarized as follows: for a particularly comprehensive identification of hollow organ systems, a method is provided for producing a digital subtraction angiography of a hollow organ system of a patient, including the following acts: providing mask image data recorded by an X-ray device; providing at least first fill image data recorded by the X-ray device, which has been recorded during an at least partial filling of the hollow organ system with a contrast agent; starting from a first intravenous and a second intraarterial contrast agent injection following in time; ascertaining at least first subtraction image data by subtracting the mask image data from the at least first fill image data; ascertaining final subtraction image data from the at least first subtraction image data; and segmenting the final subtraction image data and assigning the pixels or voxels of the final subtraction image data to at least two different intensity classes based on their respective intensity value.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for producing a digital subtraction angiography of a hollow organ system of a patient, the method comprising:
    providing mask image data recorded by an X-ray device;
    providing first fill image data recorded by the X-ray device, which has been recorded during an at least partial filling of the hollow organ system with a contrast agent, starting from a first intravenous and a second intraarterial contrast agent injection following in time;
    ascertaining first subtraction image data by subtracting the mask image data from the first fill image data;
    ascertaining final subtraction image data from the first subtraction image data; and
    segmenting the final subtraction image data and assigning pixels or voxels of the final subtraction image data to at least two different intensity classes based on a respective intensity value.

2. The method of claim 1, wherein the first subtraction image data is used as the final subtraction image data.

3. The method of claim 1, further comprising:
    providing second fill image data recorded by the X-ray device, which has been recorded during an at least partial filling of the hollow organ system with a contrast agent, starting from the first intravenous and the second intraarterial contrast agent injection following in time;
    ascertaining second subtraction image data by subtracting the mask image data from the second fill image data; and
    ascertaining final subtraction image data from the first subtraction image data and the second subtraction image data by determining a maximum intensity value of a corresponding pixel or voxel of the first subtraction image data and the second subtraction image data as an intensity value of each pixel or voxel of the final subtraction image data.

4. The method of claim 3, wherein the mask image data is formed of at least one series of projection mask images and the first fill image data and/or the second fill image data is formed of first and/or second series of projection fill images,
    wherein the series of projection mask images are reconstructed to form a mask volume and the first and/or second series of projection fill images are reconstructed to form first and/or second fill volumes,
    wherein first and/or second subtraction volumes are ascertained by subtracting the mask volume from the first and/or the second fill volume,
    wherein a final subtraction volume is ascertained from the first and/or second subtraction volume, and
    wherein the final subtraction volume is segmented, wherein the voxels of the final subtraction volume are assigned to at least two different intensity classes based on the respective intensity value.

5. The method of claim 4, wherein the at least one series of projection mask images and the at least one first and/or second series of projection fill images have been recorded during at least one rotational run of a recording system around the patient in each case.

6. The method of claim 3, wherein the mask image data is formed of at least one series of projection mask images and the first fill image data and/or the second fill image data is formed of first and/or second series of projection fill images,
    wherein first and/or second series of subtraction images are ascertained by subtracting the series of projection mask images from the first and/or the second series of projection fill images,
    wherein the first and/or second series of subtraction images are reconstructed to form first and/or second subtraction volumes,
    wherein a final subtraction volume is ascertained from the first and/or second subtraction volume, and
    wherein the final subtraction volume is segmented, wherein the voxels of the final subtraction volume are assigned to at least two different intensity classes based on the respective intensity value.

7. The method of claim 6, wherein the at least one series of projection mask images and the at least one first and/or second series of projection fill images have been recorded during at least one rotational run of a recording system around the patient in each case.

8. The method of claim 1, wherein the at least two intensity classes are differentiated by applying at least one intensity threshold value.

9. The method of claim 1, wherein the digital subtraction angiography of the hollow organ system is displayed on a display unit, and
    wherein parts of the hollow organ system assigned to different intensity classes are marked with different colors.

10. An apparatus comprising:
    a processor configured to:
        receive mask image data from an X-ray device;
        receive fill image data from the X-ray device, wherein the fill image data has been recorded during at least a partial filling of a hollow organ system with a contrast agent, starting from a first intravenous and a second intraarterial contrast agent injection following in time;
        ascertain first subtraction image data by subtracting the mask image data from the fill image data;
        ascertain final subtraction image data from the first subtraction image data; and
        segment the final subtraction image data and assign pixels or voxels of the final subtraction image data to at least two different intensity classes based on respective intensity values; and
    a memory configured to store image data.

11. The apparatus of claim 10, further comprising:
    an X-ray device configured to record the mask image data and the fill image data of a hollow organ system of a patient.

12. The apparatus of claim 11, wherein the X-ray device is a C-arm X-ray device.

13. An apparatus comprising:
    an X-ray device configured to record mask image data and fill image data of a hollow organ system of a patient;
    a processor configured to: ascertain subtraction image data by subtracting the mask image data from the fill image data; ascertain final subtraction image data; and segment the final subtraction image data and assign pixels or voxels of the final subtraction image data to at least two different intensity classes based on respective intensity values;

a memory configured to store image data; and a contrast agent injection apparatus having:
- at least two injectors arranged such that they are spaced apart from one another, wherein a first injector of the at least two injectors is configured for a triggered intravenous injection of contrast agent and a second injector of the at least two injectors is configured for a subsequent intraarterial injection of contrast agent; and
- a trigger apparatus for an automatic, controlled activation of the at least two injectors.

14. The apparatus of claim 13, further comprising:
a system controller configured to actuate the X-ray device, the processor, and the contrast agent injection apparatus.

15. The apparatus of claim 10, wherein the processor is further configured to:
receive second fill image data from the X-ray device, wherein the second fill image data has been recorded during an at least partial filling of the hollow organ system with the contrast agent, starting from the first intravenous and the second intraarterial contrast agent injection following in time;

ascertain second subtraction image data by subtracting the mask image data from the second fill image data; and ascertain the final subtraction image data from the first subtraction image data and the second subtraction image data by determining a maximum intensity value of a corresponding pixel or voxel of the first subtraction image data and the second subtraction image data as an intensity value of each pixel or voxel of the final subtraction image data.

16. The apparatus of claim 10, wherein the at least two intensity classes are differentiated by applying at least one intensity threshold value.

17. The apparatus of claim 10, further comprising:
a display unit configured to display digital subtraction angiography of the hollow organ system,
wherein parts of the hollow organ system assigned to different intensity classes are marked with different colors.

* * * * *